United States Patent [19]

Casson et al.

[11] 4,184,815
[45] Jan. 22, 1980

[54] ROLLER PUMP ROTOR WITH INTEGRAL SPRING ARMS

[75] Inventors: Melvin E. Casson, West Chester; Albert E. Moore, Mainland; George J. Berry, Sr., King of Prussia, all of Pa.

[73] Assignee: Extracorporeal Medical Specialties, Inc., King of Prussia, Pa.

[21] Appl. No.: 777,013

[22] Filed: Mar. 14, 1977

[51] Int. Cl.² .................... F04B 43/08; F04B 43/12; F04B 45/06
[52] U.S. Cl. .............................. 417/477; 128/214 F
[58] Field of Search ............... 417/477, 476, 475, 45; 418/45; 285/334.2, 236, DIG. 22, 197; 128/214 F, DIG. 3, 214 E

[56] References Cited
U.S. PATENT DOCUMENTS

| | | | |
|---|---|---|---|
| 513,316 | 1/1894 | Funk | 417/476 |
| 1,596,933 | 8/1926 | Kister et al. | 417/476 |
| 2,483,924 | 10/1949 | Moulinier | 417/477 |
| 2,899,907 | 8/1959 | Becher | 417/477 |
| 3,011,684 | 12/1961 | Corneil | 417/477 |
| 3,167,397 | 1/1965 | Skeggs et al. | 417/477 |
| 3,644,068 | 2/1972 | Lepak | 417/477 |
| 3,649,138 | 3/1972 | Clay et al. | 417/477 |
| 3,737,251 | 6/1973 | Berman et al. | 417/477 |
| 3,756,752 | 9/1973 | Stenner | 417/477 |
| 3,791,777 | 2/1974 | Papoff et al. | 417/477 |
| 3,963,023 | 6/1976 | Hankinson | 417/477 |

Primary Examiner—Carlton R. Croyle
Assistant Examiner—Thomas I. Ross

[57] ABSTRACT

A fluid pump includes an upstanding wall on its base with a generally circular rotor spaced from and generally parallel to the wall to define a tube containing path therebetween with the rotor having at least one slot which defines the inner edge of an integral spring arm upon which a roller is mounted for making depressing contact with a resilient tube mounted in the path for forcing fluid through the tube and with the integral spring arm having sufficient resiliency to accommodate any back pressure developed in the tube.

8 Claims, 10 Drawing Figures

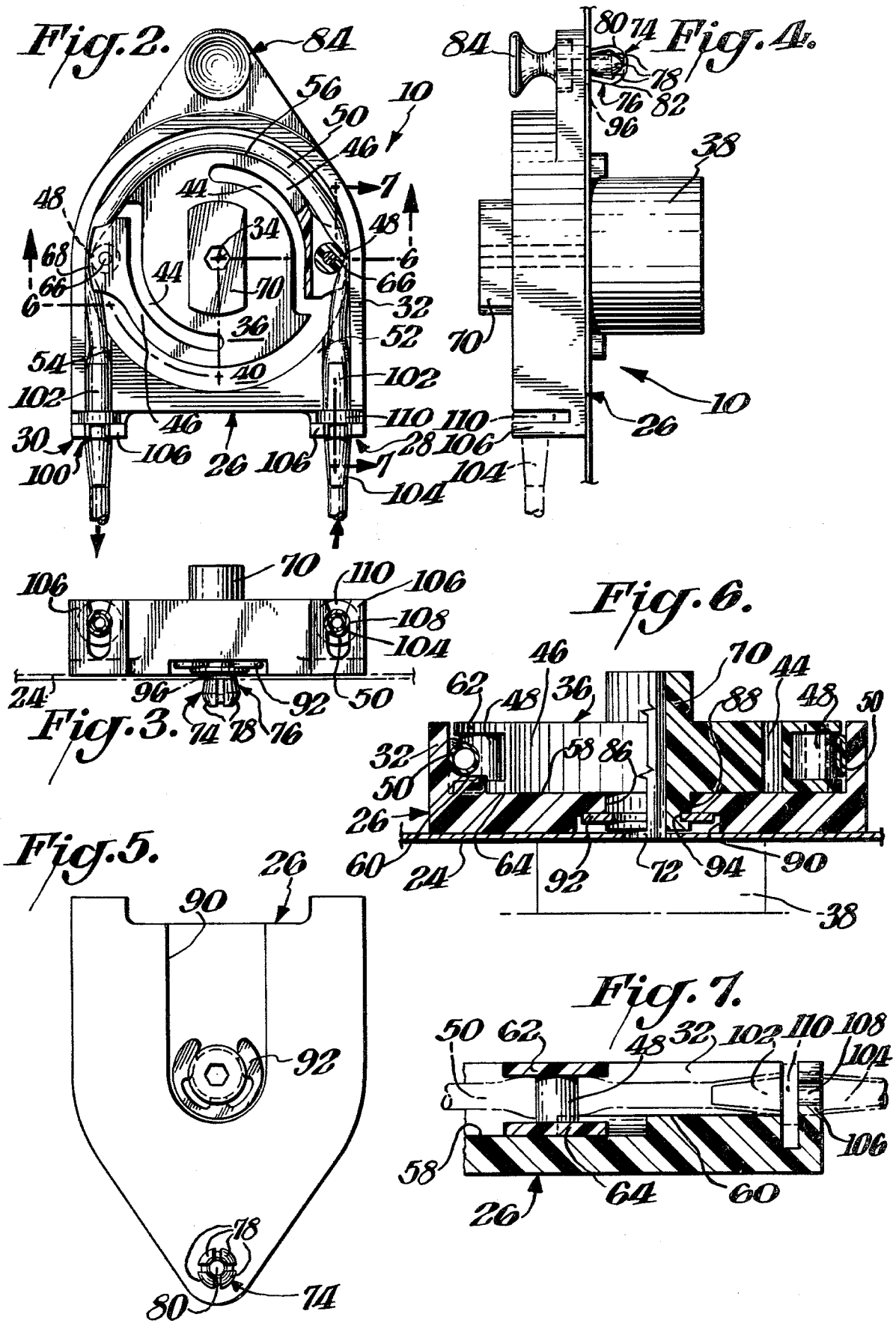

ROLLER PUMP ROTOR WITH INTEGRAL SPRING ARMS

BACKGROUND OF THE INVENTION

Fluid pumps such as peristaltic pumps are known in the art and take various forms. Commonly assigned U.S. Pat. Nos. Re. 27,376 and 3,622,252 disclose fluid pumps of the roller type which are adapted for a variety of uses but are particularly adapted for the medical profession wherein the rollers are mounted to a rotor and force fluid through a tube. Various constructional approaches have been taken in the art including the use of spring means as part of the roller mount. Exemplary of these approaches are U.S. Pat. Nos. 2,804,023; 2,909,125; 2,935,028; 3,101,675; 3,116,697; 3,122,103; 3,137,242; 3,192,863; 3,431,864; 3,644,068; 3,723,030; 3,737,251; 3,822,948; 3,832,096; 3,841,799; 3,960,466 and 3,963,023, as well as the COMPU-PET 100, MC-200P and Micron Pipetting System models distributed by Alphamedics Mfg. Corp. of Levittown, Pa. Despite these various approaches, there is a need for an effective pump of the above type which has minimal parts without sacrifice to its reliability and which lends itself to convenient use and minimal maintenance.

SUMMARY OF THE INVENTION

An object of this invention is to provide a fluid pump having a high degree of reliability as aforedescribed.

A further object of this invention is to provide such a pump of the infusion type which is particularly adapted for medical use such as for intravenous feeding.

A still further object of this invention is to provide a pump wherein a uniform dispensing of fluid is obtained for each revolution of the rotor so that a controlled dispensing can be achieved.

A yet further object of this invention is to provide such a pump which permits the use of a keyboard and display for setting and monitoring the flow.

In accordance with this invention a fluid pump includes an upstanding wall on its base with a generally circular rotor spaced from and generally parallel to the wall to define a tube containing path therebetween. The rotor has at least one slot which defines the inner edge of an integral spring arm upon which a roller is mounted for making depressing contact with a resilient tube mounted in the path for forcing fluid through the tube and the integral spring arm has sufficient resiliency to accommodate any back pressure developed in the tube.

In a preferred form of this invention the base of the pump includes an inflow station and an outflow station with the tube being mounted on the path therebetween. A coupler is provided at each of the inflow and outflow stations and the couplers are joined to the resilient tube acted upon by the pump. The opposite end of each coupler is dimensioned to receive a hose or tube of only the proper inside diameter to prevent the wrong sized hose from being mounted in the assembly and thereby otherwise upsetting the proper flow calibration.

The rotor is preferably S-shaped with a pair of integral spring arms each of which has a tube contacting roller and the dimensions are preferably selected so that for example one milliliter of flow is dispensed for each revolution of the rotor.

THE DRAWINGS

FIG. 1 schematically illustrates an assembly which includes the fluid pump of this invention for use as an intravenous infusion pump;

FIG. 2 is a top plan view of the fluid pump shown in FIG. 1;

FIG. 3 is an end elevation view of the fluid pump shown in FIG. 2;

FIG. 4 is a side elevation view of the fluid pump shown in FIGS. 2-3 and mounted on its drive motor;

FIG. 5 is a bottom plan view of the fluid pump shown in FIGS. 2-4;

Figure 8:
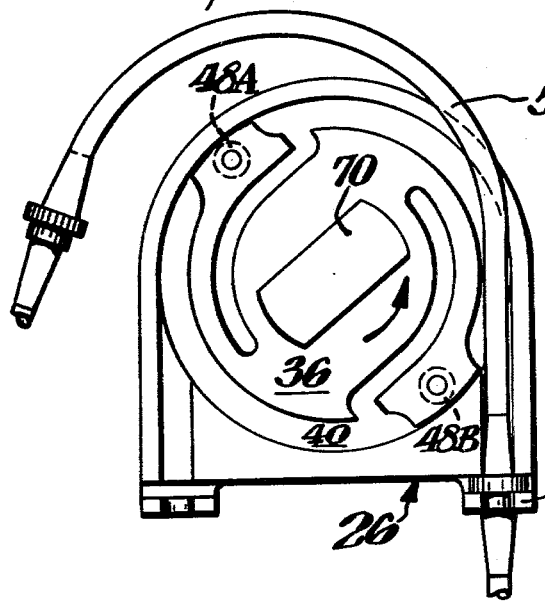
Figure 9:
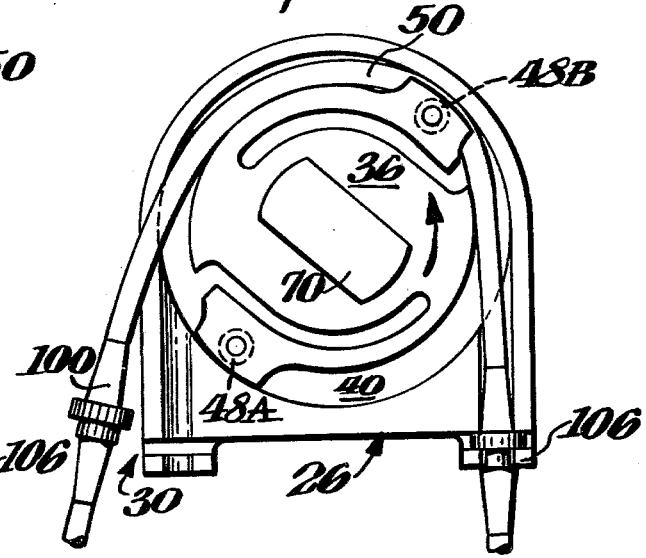
Figure 10:
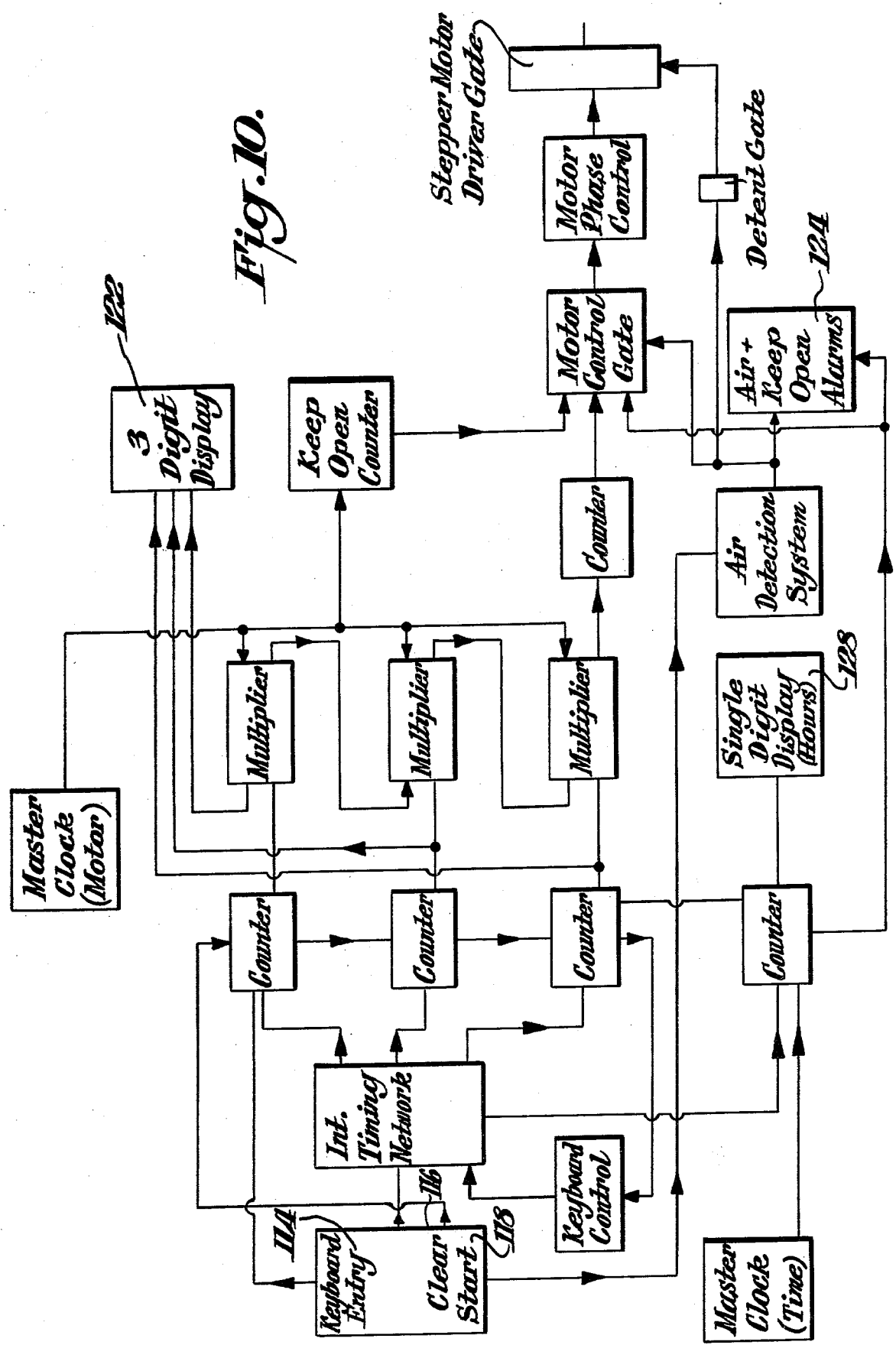

FIGS. 6 and 7 are cross-sectional views taken through FIG. 2 along the lines 6—6 and 7—7, respectively;

FIG. 8 is a plan view similar to FIG. 2 showing one of the steps for mounting the flexible tube unit in the pump;

FIG. 9 is a plan view similar to FIG. 8 showing a later step of installation; and FIG. 10 is a block diagram showing the circuitry for the fluid pump of this invention.

DETAILED DESCRIPTION

Figure 1:
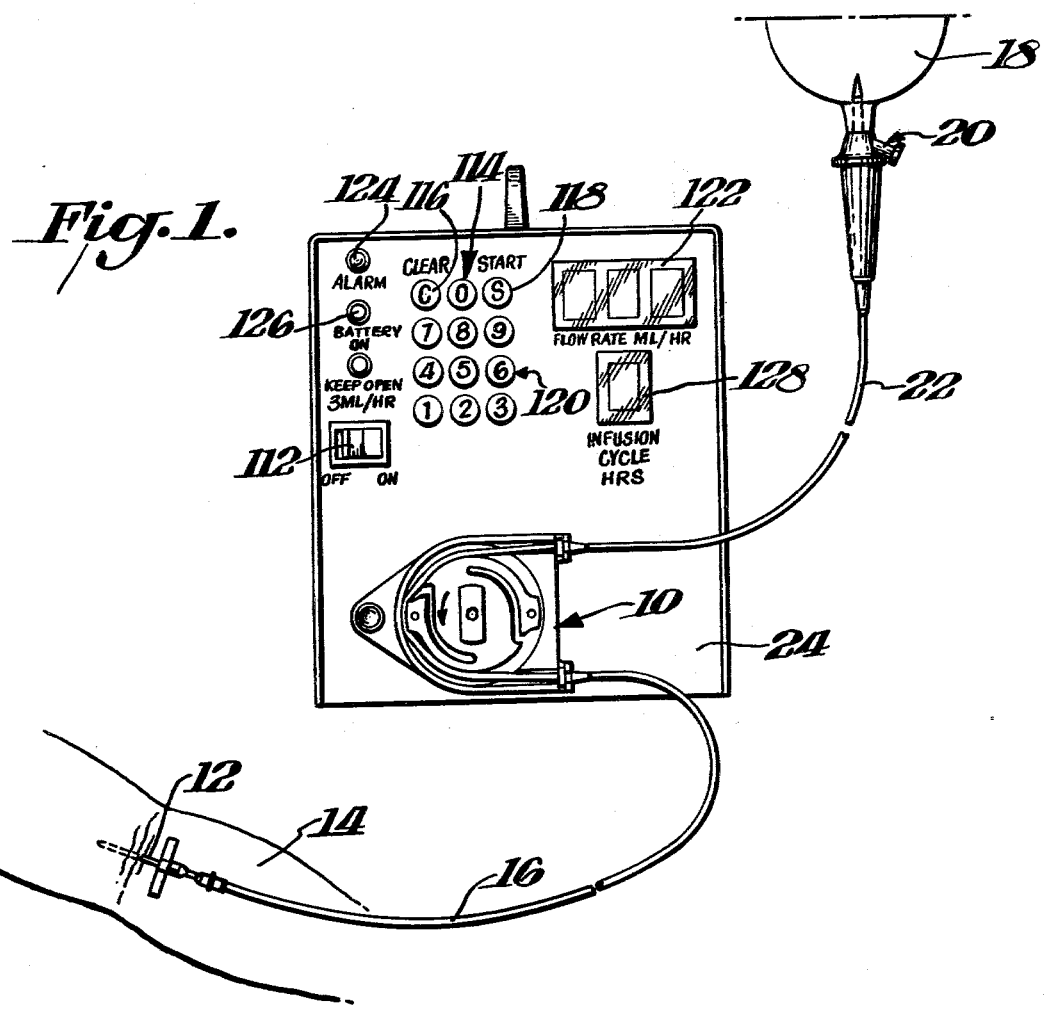

FIG. 1 illustrates a fluid pump 10 in accordance with this invention as used as an infusion pump for intravenous feeding. As indicated therein, a needle 12 or other suitable applicator is inserted into the patient 14 and is connected to outlet hose 16. Remote from applicator 12 is a source 18 of intravenous fluid which by way of conventional connecting means 20 is connected to inlet hose 22. Pump 10 acts upon the hose system to force fluid into the patient. As later described pump 10 is mounted on housing 24 which contains the necessary circuitry and drive means for the proper pumping action.

The details of pump 10 are best illustrated in FIGS. 2-7. As indicated therein pump 10 includes a base 26 having an inflow station 28 and an outflow station 30. An upstanding integral U-shaped wall 32 is disposed at the periphery of base 10 and assumes a generally U-shape with one leg of the U being at inflow station 28 and the other leg at outflow station 30. Mounted generally centrally on base 10 is a rotor 36 which includes a central aperture 34 illustrated in hexagonal shape for receiving the drive shaft 72 (FIG. 6) of a suitable drive means such as a stepping motor 38 (FIG. 4). Rotor 36 is generally circular in plan view and is mounted in a circular depression or recess 40 in base 26. Base 26 also includes an end extension 42 which in cooperation with the bight portion of upstanding U-shaped wall 32 forms the outer confines of a circular path with the inner confines being defined by the outer edge 56 of rotor 36.

As best illustrated in FIG. 2 rotor 36 is provided with a pair of mirror image slots 44 or cut-aways thereby creating integral spring arms 46 on the outer ends of which are mounted rollers 48. Rotor 36 thus assumes a generally S-shape with each end of the S being a spring arm 46 and with the arcuate outer edges 56 of the rotor being generally parallel to and spaced from the upstanding wall 32.

Resilient hose or tube 50 is located in the confined U-shaped tube containing path extending from inflow station 28 to outflow station 30. As rotor 36 rotates each roller 48 makes depressing contact with the resilient tube 50 to force fluid downstream from inflow station 28 to outflow station 30 and thus pump the fluid into the patient. The depressing action takes place from the point where roller 48 is tangential to leading edge 52 of projection 42 at the inflow station 28 and the depressing contact continues until roller 48 leaves the U-shaped path at point 54 of projection or extension 42.

The construction illustrated in FIG. 2 is particularly advantageous in that spring arms 46 have sufficient resiliency to accommodate any back pressure that might develop. Although the prior art has previously provided flow pumps with spring mounted arms the arrangement of this invention is particularly advantageous since the arms 46 are integral with rotor 36 itself and the natural or inherent resiliency of the material is utilized for the desired springiness. This integral arrangement of the rotor and its spring arms thus has the advantages of a high degree of reliability, minimal maintenance and minimal parts which can be formed or molded in the same operation.

As best shown in FIGS. 2 and 7 rotor 36 is mounted in a circular recess 40 in base 26 wherein the floor 58 of the recess 40 is at a lower level than the floor 60 of inflow station 28 and correspondingly also the floor of outflow station 30. In this manner it is possible to accommodate both the tube and the roller mounts in the limited space provided for resilient tube 50.

FIGS. 2, 6 and 7 best illustrate the mounting of rollers 48 on spring arms 46. As indicated therein, each spring arm 46 terminates in a pair of upper and lower flanges or guard surfaces 62, 64 through which pin 66 is mounted to act as a shaft for permitting rollers 48 to rotate. As best shown in FIG. 6, upper and lower guard surfaces 62, 64 extend beyond roller 48 and terminate juxtaposed upstanding wall 32. The outer edges 68 of upper and lower guard surfaces 62, 64 are arcuate to generally correspond to the arcuate shape of wall 32 and of extension 42. In this manner the tube 50 is reliably confined between the upper and lower guard surfaces 62, 64 and between roller 48 and wall 32 over the distance between inflow station 28 and outflow station 30.

Rotor 36 also includes an integral boss 70 centrally mounted thereof which serves as a handle for manual manipulation of the rotor as desired. Axial opening 34, likewise, extends through boss 70 to thereby extend the bearing surface for the drive shaft 72 of motor 38 (FIG. 6).

Pump 10 is secured to housing 24 by means of the mounting of drive shaft 72 through central aperture 34 and also by means of a split snap pin assembly 74 best illustrated in FIGS. 3 and 4. Snap pin assembly 74 includes a split casing 76 having a series of individual spring legs 78. Mounted within the split casing 76 is a longitudinally movable actuating rod 80 terminating in an enlargd bulb portion 82 so that upon depressing rod 80 by means of finger support 84 bulb 82 causes spring legs 78 to spread apart. For installation rotor 36 is inserted through a central opening 86 in base 26 until its central projection 88 extends beyond opening 86 in the recess 90 provided therefor. A conventional ring 92 or other suitable locking means is then applied to annular groove 94 in rotor extension 88 to lock the rotor in place against axial movement while still permitting it to rotate. The assembly consisting of rotor 36 and base 26 is then mounted on housing 24 with motor drive shaft 72 being inserted in hole 34 of rotor 36. At the same time casing 76 is inserted through a corresponding opening 96 (FIG. 4) of housing 24 and rod 80 is depressed to force spring legs 78 apart thereby locking pump 10 to housing 24.

A particularly advantageous feature of this invention is that the dimensions are so selected as to assure uniform dispensing of fluid for each revolution of rotor 36. Preferably, for example each revolution of the rotor results in the dispensing of one milliliter (ml) of fluid. This correlation of rotor revolution to fluid dispensing is provided by selecting the proper tube size (i.e., inside diameter or area) of tube 50 in relation to the path of roller 48 during which the dispensing action takes place. By so selecting these dimensions it is possible to provide for a convenient quantity, such as a whole integer and preferably one milliliter, of fluid to be dispensed so that by varying the speed of rotation the amount of fluid dispensed can be likewise varied without the necessity of resorting to complicated charts, equations, etc.

The fluid pump 10 of this invention also provides means to assure that once the dispensing correlation has been established the correlation will not be destroyed by the use of improperly sized tubing. In this respect hose 50 is initially selected to provide the aforedescribed proper correlation. Hose 50 is a separate element of the general tubing system and is of a length to extend only from inflow station 28 to outflow station 30. The remaining portions of the tubing system, namely, hoses 16 and 22 are established in flow communication with tube 50 by means of couplers 100 provided at inflow station 28 and outflow station 30. Each coupler includes a pair of nipples 102, 104. Each end of tube 50 is mounted over a nipple 102, while hoses 16, 22 are mounted over nipples 104. Nipples 104 in turn are so dimensioned as to accept only the proper size hose 16, 22 which will be compatible with the flow of fluid through preselected sized tube 50. Thus by providing these properly sized nipples 104 on couplers 100 there is assurance that hoses 16, 22 will not be too small or too great so as to destroy the calibration which is established by the size of tube 50 and the path length of rollers 48.

FIGS. 2-3 and 6 best illustrate the manner in which couplers 100 are secured to base 26. As indicated therein each of inflow station 28 and outflow station 30 includes a pair of forwardly disposed spaced parallel resilient upstanding legs 106 which are spaced a slight distance beyond base 26 proper. Legs 106 include arcuate coupler receiving indentations or recesses 108 (FIG. 3) therein. Couplers 100 in turn are provided with circular flanges 110 dimensioned to fit in the space between legs 106 and base 26. For installation flange 110 is disposed in the space and the coupler is squeezed downwardly thus spreading the legs 106 apart until coupler 100 snaps into recesses 108 thereby locking the couplers in place.

Advantageously, the various components of pump 10, namely, base 26 with its upstanding legs 106 and rotor 36 with its integral spring arms 46 and handle 70 and locking arrangement 74, are all made of the same material and preferably a material such as Delrin which has the requisite springiness and memory characteristics and which lends itself to mass production by, for example, molding. Other materials, however, may also be used to obtain the desired results.

FIGS. 8-9 illustrate the steps in inserting the tubing system in pump 10. Tube 50 is mounted on the couplers 100 and hoses 16 and 18 are secured to nipples 104 of couplers 100. By manipulation of handle 70 rotor 36 is rotated so that for example, as shown in FIG. 8, neither of the rollers 48 is disposed at the general area downstream from inflow station 28 with one roller 48B, for example, being immediately upstream from inflow station 28. Inflow station coupler 100 is then snapped into legs 106 and tube 50 is disposed in the confined path between rotor 36 and wall 32 until the tube is in the general area of downstream roller 48A (as shown in FIG. 8). By manipulating handle 70 rotor 36 is then rotated counterclockwise until the downstream roller 48A just passes outflow station 30. During this rotation upstream roller 48B is making depressing contact with tube 50 and the components assume the general location illustrated in FIG. 9. As is apparent from FIG. 9, the path from roller 48B to outflow station 30 is thus clear permitting the remaining portion of tube 50 to be inserted in the confined path and the outflow coupler 100 to be snapped into legs 106 whereupon the components assume the condition illustrated in FIG. 2 and the unit is ready for operation.

A further advantage of this invention is that pump 10 permits the use of a keyboard and display for setting and monitoring the flow. As illustrated in FIG. 1 housing 24 includes an actuating on/off button 112 and also includes a set 114 of twelve individual buttons. Ten of these buttons are numbered from zero to nine. These ten buttons may be referred to as the set of numbered buttons 120. Another of the buttons 116 is used for clearing any previous settings and the final button 118 is used for start. By means of the circuitry schematically illustrated in FIG. 10 the numbered buttons 120 may be actuated to set the flow rate in, for example, milliliters per hour. This is accomplished by the incorporation of stepping motor 38 and the actual flow rate achieved is visually displayed by LED display unit 122. The unit also includes alarm 124 for warning of malfunctions and includes battery on signal 126 as well as display 128 for the number of hours or infusion cycle.

Fluid pump 10 thus provides a unit which may be conveniently used without the necessity of compiling charts or equations by simply punching in the desired fluid flow rate with assurance from the display unit that such flow rate is achieved. The unit is made of minimal parts with maximal use of integral components thus minimizing the maintenance requirements while enhancing the reliability thereof.

What is claimed is:

1. A fluid pump comprising a base, an upstanding wall on said base, a rotor rotatably mounted on said base, drive means for rotating said rotor, said rotor being formed from a plastic material in a generally circular shape in its plan view with an outer wall generally parallel to and spaced from said upstanding wall to define a tube containing path therebetween, a resilient tube fixedly disposed in said path, said rotor containing at least one integral spring arm formed therein by removing material from the generally circular rotor in the form of an arcuate slot extending inwardly from the periphery of said rotor along a path substantially parallel to the periphery of the rotor, a roller mounted on said spring arm and disposed at least partially in said path for making depressing contact with the resilient tube for forcing fluid through the tube as said rotor is rotated by said drive means, and said integral spring arm being sufficiently resilient to accommodate any back pressure developed in the tube.

2. The pump of claim 1 including an inflow coupler mounted at an inflow station mounted on said base, an outflow coupler mounted at an outflow station mounted on said base, the resilient tube connected to and between said couplers.

3. The pump of claim 2 wherein each of said couplers has a nipple disposed away from said resilient tube, said nipples being dimensioned for receiving only the proper size inlet and outlet hoses therein to assure the dispensing of said fixed amount of fluid.

4. The pump of claim 3, in combination therewith, an inlet hose mounted on said nipple at said inflow station, connecting means on said inlet hose for connection to a supply of intravenous fluid, an outlet hose mounted on said nipple at said outflow station, and intravenous applicating means on said outlet hose for insertion into a living body to discharge the fluid therein.

5. The pump of claim 1 wherein the inside cross-sectional flow area of said resilient tube is related to the path of travel of one revolution of said rotor to dispense a fixed amount of fluid from said tube.

6. The pump of claim 1 wherein a pair of diametrically disposed integral spring arms are formed in said rotor with a roller on the end of each of said arms.

7. The pump of claim 6 wherein said rotor is generally S-shaped with the free ends of the S comprising a pair of diametrically disposed spring arms, coupling means on said base remote from said rotor for connection to a support, each of said spring arms terminating in a channel section having a pair of upper and lower guard surfaces, one of said rollers being mounted to and between a respective of said pair of guard surfaces, said guard surfaces extending beyond its said roller and terminating in arcuate edges juxtaposed said upstanding wall to confine the tube therebetween and between its said roller and said upstanding wall, said upstanding wall being generally U-shaped, said rotor being located in a circular depression in said base said rotor having a central boss which comprises a handle therefore, and an axial opening in said rotor for receiving a motor drive shaft of said drive means.

8. The pump of claim 6 wherein said base and said rotor are made of the same material.

* * * * *